United States Patent [19]

Gibbs

[11] 3,949,067

[45] Apr. 6, 1976

[54] SHAVING LUBRICANT
[76] Inventor: Harold E. Gibbs, 3039 W. 39th St. No. 2017, Indianapolis, Ind. 46208
[22] Filed: June 14, 1974
[21] Appl. No.: 479,289

[52] U.S. Cl. ....................... 424/73; 83/22; 424/364
[51] Int. Cl.² ............................................ A61K 7/15
[58] Field of Search ............ 424/73; 83/22; 424/364

[56] References Cited
UNITED STATES PATENTS
2,987,446   6/1961   Riethmüller ...................... 424/73 X FOREIGN PATENTS OR APPLICATIONS
1,209,595   10/1970   United Kingdom .................. 424/73
1,150,180   6/1963   Germany ............................ 424/73

OTHER PUBLICATIONS
Bennett, Cosmetic Formulary, The Chemical Publishing Co., New York, N.Y.; (1937); pp. 208–209.

*Primary Examiner*—Stanley J. Friedman
*Assistant Examiner*—Vera C. Clarke
*Attorney, Agent, or Firm*—Jenkins, Hanley & Coffey

[57] ABSTRACT

A shaving lubricant which consists essentially of approximately 3 parts by volume of distilled white vinegar and approximately one part of citrus fruit juice. In an optimum form, the fruit juice is approximately one-half lemon juice and one-half lime juice and approximately 100 International units of vitamin E are dissolved in approximately four liquid ounces of the liquid mixture. A method of shaving wherein the area to be shaved is lathered, a sharpened edge of a razor blade is liberally sprayed with the lubricant, and the sprayed blade edge is used to shave the lathered area, respraying the blade edge after each removal of lather therefrom.

6 Claims, No Drawings

SHAVING LUBRICANT

For centuries, one of the onerous and unpleasant burdens to which mankind has been subjected is the removal of unwanted hair, primarily from the face and frontal neck. For most men, the task must be performed at least once every day and for most men who use a blade, whether "straight-edge" or "safety," the skin is nicked, sliced or superficially scraped at least once during almost every shave.

During relatively recent decades, a great many women have turned to shaving for removal of unwanted hair on the legs and/or arms; and they encounter the same sorts of objectionable incidents.

Therefore, mankind has long sought any means for amelioration of the discomforts which have always accompanied shaving and many expedients have been tried with greater or lesser degrees of success.

I have discovered that a lubricant consisting essentially of vinegar approximately three parts by volume and citrus fruit juice approximately one part by volume, when applied to the shaving edge before, and preferably during, the shaving operation, very significantly reduces discomfort of the shaving operation by minimizing the "pull" of the blade, permitting longer shaving strokes, greatly increasing the truly sharp life of a blade and very significantly reducing the nicks, cuts and chafing which otherwise would occur during the act of shaving.

Preferably, I use a commercial distilled, white vinegar which is labeled "Reduced with water to 4% acidity (40 gr.)" but I presently believe that any white, distilled vinegar readily available on the market will perform substantially as well. Preferably, as the citrus fruit juice I use a commercial reconstituted lemon juice which is labeled "Filtered water, lemon concentrate with 0.1% sodium benzoate and 1/50% sodium disulfite."

After the area to be shaved is lathered in accordance with customary practice, I apply the above mixture liberally to a sharpened edge of the blade to be used and then proceed to shave the lathered area in the usual manner, but applying a further amount of the described lubricant to the blade edge after each removal of lather from the blade edge. The lubricant can be applied in any way but is preferably sprayed from a pump-type spray contaner onto the blade.

I have found that, among a number of persons who have used the lubricant in this manner, the results have been uniform — smoother, more comfortable shaves with almost no nicking, cutting or chafing of the skin, and much longer blade life. One individual with a heavy, dark beard has found it necessary, throughout his adult life, to shave a second time on any occasion when he wished to enjoy a social evening; and, since he has been using the above procedure, he has found that his morning shave will last satisfactorily throughout a social evening.

A modification of the above formula in which the cirtus fruit juice was one-half reconstituted lemon juice and one-half reconstituted lime juice appears to give even better results in all of the above-mentioned phases.

I have found, further, that the addition of approximately one-hundred International units of vitamin E dissolved in approximately four liquid ounces of the above mixture produces optimum results with a very noticeable improvement in the frequency of nicking, cutting or chafing the skin.

The reconstituted citrus juice which I have used is a concentrate such as is well known on the market, and I use the product without water dilution.

I claim as my invention:

1. A shaving lubricant consisting essentially of, by volume approximately 3 parts distilled white vinegar and approximately one part lemon juice.

2. The lubricant of claim 1 in which the lemon juice is reconstituted.

3. A shaving lubricant consisting essentially of, by volume, approximately 3 parts distilled white vinegar and approximately one part citrus fruit juice, said fruit juice being approximately one-half lemon juice and one-half lime juice.

4. The lubricant of claim 3 in which the juices are reconstituted.

5. The lubricant of claim 1 also including approximately one hundred International units of Vitamin E in approximately four liquid ounces of the vinegar and lemon juice.

6. The lubricant of claim 3 also including approximately one hundred International units of Vitamin E in approximately four liquid ounces of the vinegar and citrus fruit juice.

* * * * *